US006524255B2

United States Patent
Pawluskiewicz

(10) Patent No.: US 6,524,255 B2
(45) Date of Patent: Feb. 25, 2003

(54) ACOUSTIC COUPLING GUIDE FOR AN ULTRASONIC TRANSDUCER PROBE

(75) Inventor: Peter M. Pawluskiewicz, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 51 days.

(21) Appl. No.: 09/735,428

(22) Filed: Dec. 12, 2000

(65) Prior Publication Data

US 2002/0072675 A1 Jun. 13, 2002

(51) Int. Cl.[7] .................................................. A61B 8/00
(52) U.S. Cl. ........................ 600/459; 600/460; 600/461
(58) Field of Search ................................. 600/443, 447, 600/460, 459, 461, 462, 463, 437

(56) References Cited

U.S. PATENT DOCUMENTS 4,817,616 A    4/1989   Goldstein
6,099,464 A  * 8/2000   Shimizu et al. ............. 600/104
6,149,598 A  * 11/2000  Tanaka ........................ 600/437
6,165,127 A  * 12/2000  Crowley ...................... 600/439
6,217,528 B1 * 4/2001   Koblish et al. ............. 600/585

* cited by examiner

Primary Examiner—Francis J. Jaworski
Assistant Examiner—Maulin Patel
(74) Attorney, Agent, or Firm—W. Brinton Yorks, Jr.

(57) ABSTRACT

A coupling guide is provided for controlling the shape and size of a condom covered medical diagnostic ultrasound probe. The coupling guide maintains a constant distance between the transducer of the probe and the surface being examined by controlling the shape and size of the condom as it is inflated with a fluid. The coupling guide of the present invention can also be used to keep an organ stabile while the organ is being scanned and minimizes discomfort to the patient.

15 Claims, 3 Drawing Sheets

ACOUSTIC COUPLING GUIDE FOR AN ULTRASONIC TRANSDUCER PROBE

This invention relates to ultrasonic diagnostic imaging system probes that require the use of a coupling material, in particular to a guide for controlling the size and shape of the coupling material.

Ultrasonic diagnostic imaging systems are in widespread use for performing ultrasonic imaging and measurements of the human body through the use of probes which may be placed internal or external to the body being measured. The probes are used to view the internal structure of a body by creating a scan plane. The scan plane is produced from an array of transducers that transmit pulses or beams of energy into the body and receive returning echoes of energy as they are reflected from internal structures of the body. The scan plane is essentially the field of view inside the body being measured.

Probes that are inserted into the body for scanning, such as transrectal and transvaginal probes, often require the use of a coupling material between the transducer and the surface being examined. Such probes may have multiple transducers mounted in different positions at the distal end of the probe to obtain multiple scan planes. The transducer may also be rotatable in the distal end of the probe to provide multiple scanning planes.

Coupling materials emulate body tissue and are important in scanning a surface that is in close contact with the surface of the transducer. In such cases, the coupling material acts as a standoff, which allows the transducer to focus on the surface being examined. The coupling material must be placed between the transducer and the surface being examined to create a constant gap or distance that emulates body tissue. If a constant distance is not maintained between the transducer and the surface being examined, then the image quality of the scanned region may become diminished as the probe is unable to focus on tissues close to the transducer.

In procedures such as prostate brachytherapies or biopsies, the prostate gland is scanned with a probe that is inserted into the rectum of the patient being examined. The user of the probe may insert a needle into the prostate to deposit radioactive seeds or to take samples of cellular material. The probe is used to obtain an image of the prostate and an image of the needle while it is inserted in the prostate. The probe can also be used to stabilize or hold the prostate still by applying pressure to the interior wall of the rectum. A coupling material is typically used in such applications to keep a constant distance between the transducer and the interior wall of the rectum. There are currently several methods for using coupling materials on probes; however, there are problems associated with each method.

One type of coupling material is a block of soft silicon that is placed over the transducer to create a spacer between the transducer and the surface being examined. The silicon spacer typically extends an eighth of an inch or more from the face of the transducer and thus increases the diameter of the probe by the same amount. Since the structure of the silicon spacer is generally firm, a constant distance is maintained between the transducer and the surface being examined, even as pressure is applied to the silicon spacer. The constant distance created by the silicon spacer permits the user to manipulate or maneuver the probe within the rectum without distorting the focus of the transducer. The user can also use the spacer to stabilize the prostate by applying pressure to the interior wall of the rectum.

A drawback to a silicon spacer is that it is attached to the probe before it is inserted into the body. The size of the silicon spacer adds to the size of the probe, and the patient being examined may incur discomfort or pain when the probe and silicon spacer are inserted into the body. Also, once the probe and spacer are inside the body, the distance between the transducer and the surface being examined cannot be modified by the user without removing the probe from the body and re-inserting the probe with a different size silicon spacer.

Prophylactic materials or condoms filled with water are currently used to eliminate the discomfort caused by silicon spacers. In such applications, a condom is placed over the probe and sealed at one end before it is inserted into the body. Once the condom covered probe is inserted into the body, water may be introduced into the probe through an external port on the probe. Since the condom is sealed at one end, the condom inflates when the water is introduced. The water filled condom creates an acoustic coupling between the transducer and the surface being scanned.

Since the outer surface of the condom is unrestricted, the condom expands over its entire surface area as more water is introduced into the condom. For example, in prostate procedures, the condom is typically inflated until the entire rectum is filled. When the condom is inflated in such a manner, the condom conforms to the interior walls of the rectum and becomes stationary while the probe moves freely within the condom. Not only does such a method cause discomfort to the patient, the free movement of the probe creates several problems.

As stated above, it is desirable to maintain a constant distance between the transducer and the surface being examined to keep the transducer focused. The water-filled condom provides no resistance against the probe and thus allows the probe to come into contact with, or in close proximity to, the condom itself. In such cases, the coupling effect of the water is eliminated. Moreover, a probe with an inflated condom around its circumference cannot be used to stabilize an organ while the organ is being scanned by the probe. To stabilize an organ such as a prostate, the probe must be pressed against the interior wall of the rectum. However, as soon as the probe is pressed against the interior wall of the rectum, the water coupling is eliminated due to the lack of resistance from the water.

Also, since the probe moves freely within the condom, it is difficult to maintain a constant distance between the transducer and the surface being examined. If the distance varies while the probe is scanning, then the probe becomes unfocused and the image quality of the scanned region may become diminished.

Accordingly, it is desirable to have a guide for controlling the size and shape of coupling material while also maintaining a constant distance between the transducer and the surface being examined. The guide should maintain the constant distance even if the probe is moved during the scanning procedure. It is also desirable to have a guide that will allow the coupling material and probe to be used to keep an organ stable while the organ is being scanned. It is also desirable to have a guide that minimizes discomfort to the patient.

In accordance with the principles of the present invention, a coupling guide is provided for controlling the size and shape of a condom covered probe when the condom is inflated with a fluid such as water. The inflated portion of the condom maintains a constant distance between the transducer and the surface being examined, even if the probe is moved during the scanning procedure. The present invention allows an inflated condom and probe to be used for stabilizing organs while the probe is scanning the organ. The present invention also minimizes discomfort to the patient.

Figure 1:
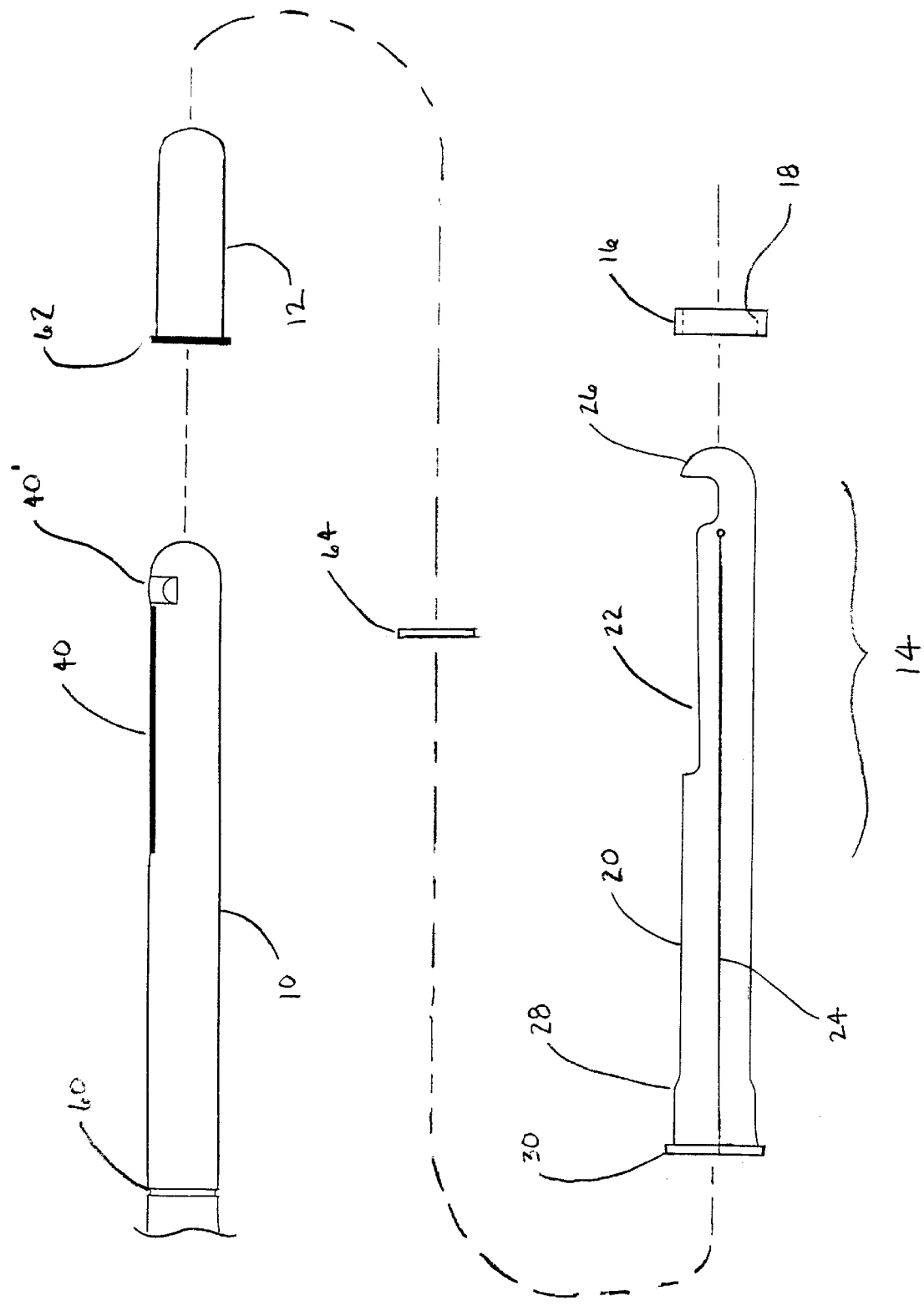
FIG. 1 shows the configuration and assembly of a coupling guide of the present invention.

Referring first to FIG. 1, the assembly of a coupling guide of the present invention is shown. Probe 10 is shown with two transducers 40 and 40' ortheogonally oriented to image orthogonal planes within the body, however, it will be apparent to those skilled in the art that the present invention may be modified to accommodate one or more transducers in varying configurations. Probe 10 is also shown with groove 60. Condom 12 is shown with an unrolled portion of the condom or end-ring 62. Guide 14 is comprised of body 20, opening 22, optional slit 24, and locking ring 16. Body 20 is shown as being cylindrical shaped, having a closed-end 26, flared-end 28, and an end-piece 30.

Optional slit 24 is shown along the longitudinal axis of body 20 for easing the insertion of body 20 over probe 10 and condom 12. Slit 24 allows body 20 to be closely matched in size to probe 10 such that body 20 will fit snugly over probe 10 and condom 12. Locking ring 16 is also shown having inside diameter 18, which is slightly smaller than the outer diameter of flared-end 28 and smaller than the outer diameter of end-piece 30 to provide a stop for locking ring 16. Guide 14 may be made from a flexible bio-compatible material such as polysulfone and may be disposable.

To assemble the coupling guide of the present invention, condom 12 is unrolled over probe 10 until end-ring 62 is positioned in groove 60. If the user desires to unroll condom 12 past groove 60, then optional o-ring 64 may be placed in groove 60. Body 20 is then positioned over condom 12 such that opening 22 is over transducers 40 and 40' and flared-end 28 covers end-ring 62. Locking ring 16 is then slid over body 20 from closed-end 26 towards flared-end 28. As locking ring 16 is positioned over flared-end 28 and butted against end-piece 30, end-ring 62 will be compressed between groove 60 and body 20. Locking ring 16 will also become removably secured over groove 60, end-ring 62, and body 20 to create a water tight seal.

Figure 2:
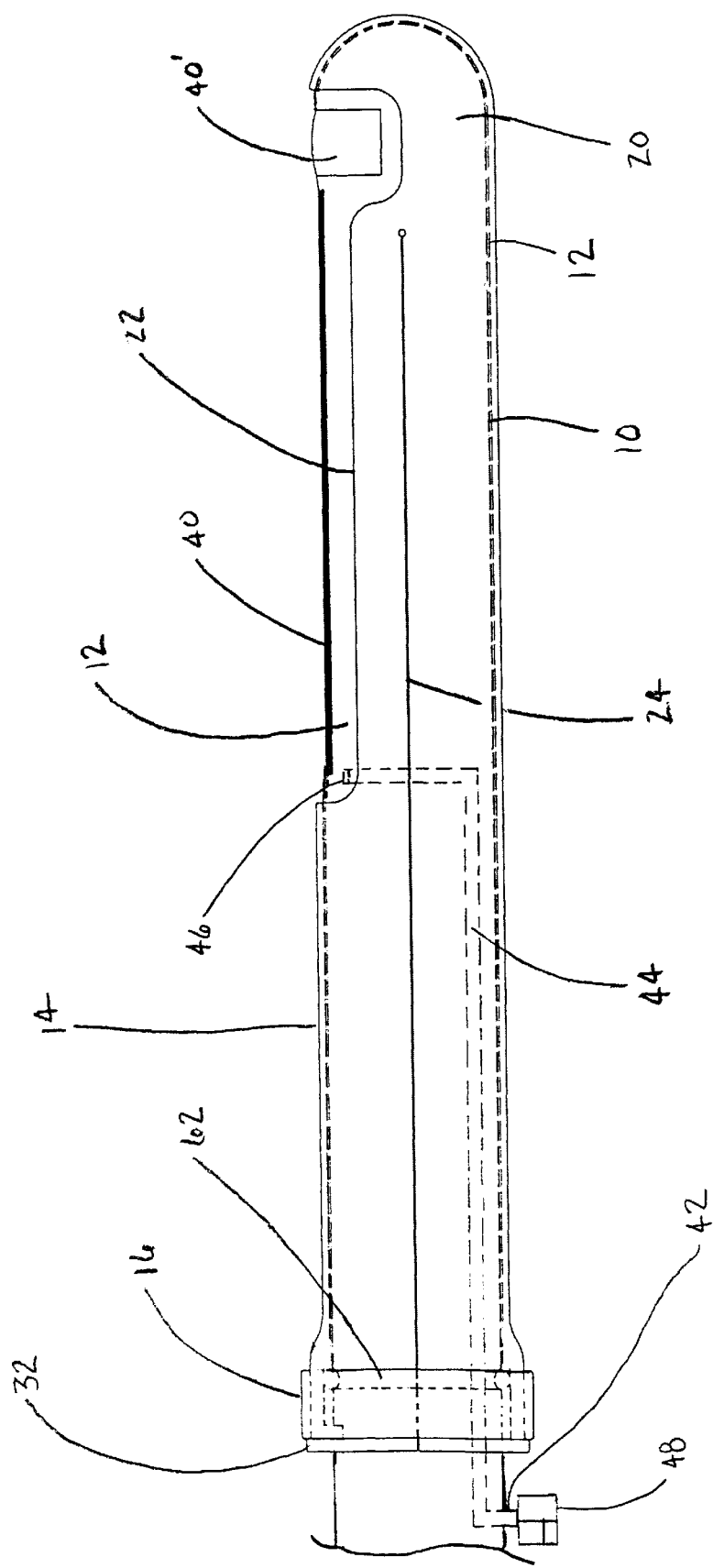
FIG. 2 shows a coupling guide of the present invention attached to an ultrasonic probe.

Referring next to FIG. 2, probe 10 is shown covered with condom 12 and guide 14. Also shown in FIG. 2 are inlet 42, conduit 44, outlet 46, and control valve 48. Conduit 44 runs from inlet 42 through the interior chamber of probe 10 to outlet 46.

Once guide 14 is secured to probe 10, the user may insert the probe into the body of the patient. After the probe is inside the body, the user may introduce water into inlet 42 from a water source such as a syringe (not shown). If a syringe is used as the water source, the user can draw trapped air out of conduit 44 prior to introducing the water. As the water is introduced into inlet 42, the water will travel through conduit 44 until it exits outlet 46. Since outlet 46 is exposed to the area between probe 10 and the inside of condom 12, the condom will expand as more water is introduced.

Figure 3A:
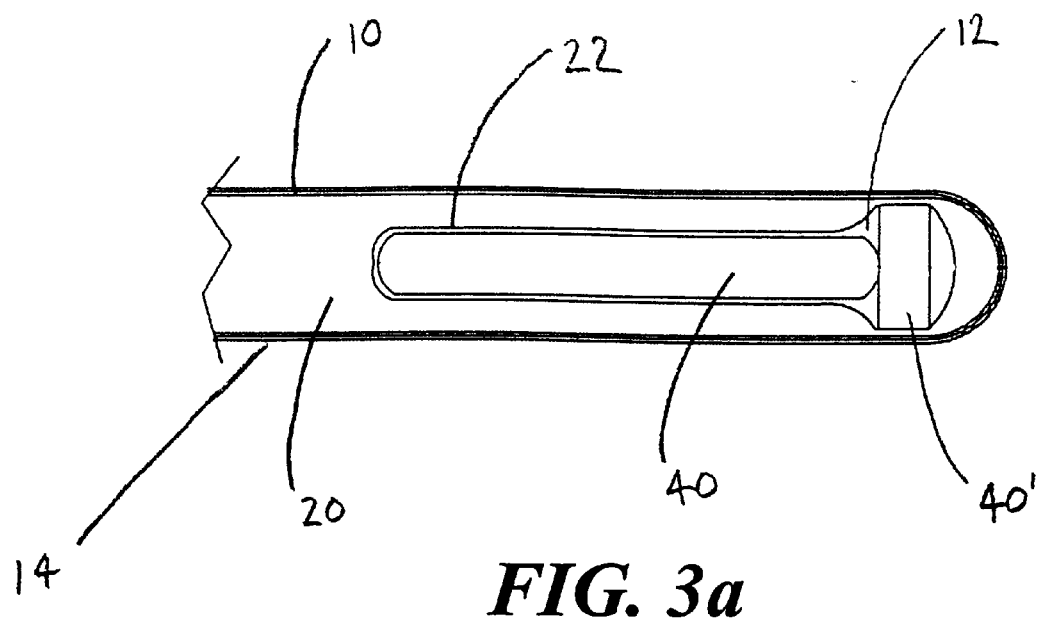
FIGS. 3a and 3b show top and side views of a coupling guide of the present invention.
Figure 3B:
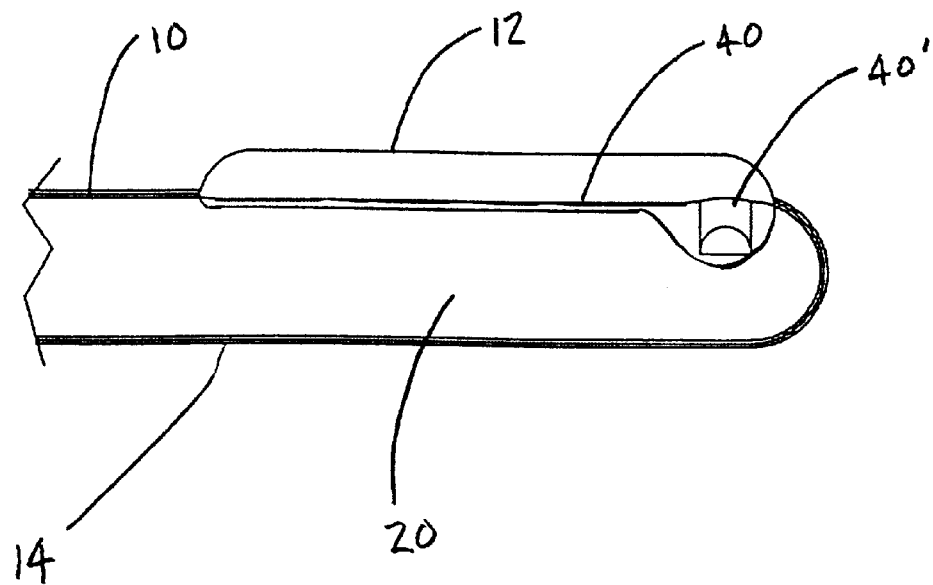

As water is introduced, condom 12 will only expand through opening 22 because the remaining portion of condom 12 is restricted by body 20 (See FIGS. 3a and 3b). Probe 10 may now be used in a manner similar to a silicon spacer, as described above, without the drawbacks of the silicon spacer. Control valve 48 may be used between inlet port 42 and the water source (not shown) to control the flow rate of water or to permit the water source to be disconnected after water is introduced.

Referring now to FIG. 3a, a top view of probe 10 is shown covered with condom 12 and guide 14. Opening 22 is shaped to conform to transducers 40 and 40' such that no portion of body 20 obstructs or interferes with the scan plane of the transducers.

Referring now to FIG. 3b, a side view of guide 14 is shown. Probe 10 is shown with condom 12 after it has been inflated with water. Since condom 12 can only expand through opening 22 as it is inflated with water, an acoustic coupling path of water is formed over transducers 40 and 40' rather than around the entire circumference of probe 10. Inflated condom 12 can be used to apply pressure to an organ such as the prostate through the interior wall of the rectum while the probe is scanning the prostate. The pressure can be applied with probe 10 and inflated condom 12 or by increasing the size of condom 12.

The size of the standoff formed by the inflated condom 12 can be increased during any procedure by introducing more water through inlet 42 (See FIG. 2). The water standoff can also be decreased in size during any procedure by draining water from inlet 42 (See FIG. 2). Once condom 12 is inflated to the desired size, condom 12 will provide a standoff of constant distance between the transducer and the surface being examined, thus providing the advantages of the silicon spacer with minimal discomfort to the patient.

What is claimed is:

1. A coupling guide for guiding and controlling the path of a fluid inserted into a medical diagnostic ultrasound probe having a transducer and having a flexible material between said guide and said probe for containing said fluid, comprising:

a body shaped to conform to said probe and having an opening aligned with said transducer for guiding and controlling the shape and size of said flexible material.

2. The coupling guide of claim 1, further comprising means for expanding said flexible material with a fluid while said probe is inserted in a body being examined.

3. The coupling guide of claim 2, wherein said body provides a slit for snugly fitting said body over said probe.

4. The coupling guide of claim 2, further comprising fastening means comprising a locking ring having an inside diameter slightly smaller than the outer diameter of said body.

5. The coupling guide of claim 4, further comprising a seal formed by said flexible material compressed between a groove in said probe and said body.

6. The coupling guide of claim 4, wherein said seal is comprised of an o-ring compressed between a groove in said probe and said body.

7. A medical diagnostic ultrasound probe comprising:

a longitudinal member having a transducer located at a distal end of said longitudinal member;

a flexible material covering said longitudinal member and overlaying said transducer; and means for controlling the shape and size of said flexible material overlaying said transducer, wherein said flexible material is positioned between said longitudinal member and said means for controlling the shape and size of said flexible material.

8. The ultrasonic probe of claim 7, wherein said means for controlling the shape and size of said flexible material is comprised of a body shaped to fit snugly over said longitudinal member and a locking ring for removably securing and sealing said body to said probe over said flexible material.

9. The ultrasonic probe of claim 8, wherein said body is comprised of an opening for expansion of said flexible material.

10. The ultrasonic probe of claim 9, wherein said opening is shaped to align with said transducer for unobstructed scanning by said transducer.

11. The ultrasonic probe of claim 8, wherein said seal is comprised of said flexible material between a groove in said probe and said body.

12. The ultrasonic probe of claim 8, wherein said seal is comprised of an o-ring compressed between a groove in said probe and said body.

13. A medical diagnostic ultrasound probe for inter-cavity scanning of a body having a longitudinal member with a distal end, an outer surface, and an inner chamber comprising:

a transducer located at said distal end of said longitudinal member;

a conduit extending from said outer surface through said inner chamber, having an inlet and outlet;

a flexible material positioned over said outer surface and overlaying said transducer;

a body, shaped to fit snugly over said longitudinal member and said flexible material, having an opening aligned with said transducer, wherein said flexible material is positioned between said body and said longitudinal member; and fastening means for removably securing said body over said flexible material and said probe to create a seal.

14. The medical diagnostic ultrasound probe of claim 13, wherein said opening is sized for guiding and controlling the shape and size of said flexible material while said fluid is within said flexible material.

15. The medical diagnostic ultrasound probe of claim 13, wherein said body provides a slit along the longitudinal axis of said body.

* * * * *